(12) United States Patent
Pritchard (10) Patent No.: US 11,383,037 B2
(45) Date of Patent: Jul. 12, 2022

(54) MULTICHAMBERED SYRINGE

(71) Applicant: Bryson Pritchard, Palmyra, VA (US)

(72) Inventor: Bryson Pritchard, Palmyra, VA (US)

( * ) Notice: Subject to any disclaimer, the term of this patent is extended or adjusted under 35 U.S.C. 154(b) by 553 days.

(21) Appl. No.: 16/455,926

(22) Filed: Jun. 28, 2019

(65) Prior Publication Data

US 2019/0314576 A1 Oct. 17, 2019

Related U.S. Application Data

(60) Provisional application No. 62/753,401, filed on Oct. 31, 2018.

(51) Int. Cl.
| | | |
|---|---|---|
| *A61M 5/19* | (2006.01) | |
| *A61M 5/315* | (2006.01) | |
| *A61M 5/28* | (2006.01) | |
| *A61M 5/178* | (2006.01) | |

(52) U.S. Cl.
CPC .......... *A61M 5/19* (2013.01); *A61M 5/31596* (2013.01); *A61M 5/284* (2013.01); *A61M 2005/1787* (2013.01)

(58) Field of Classification Search
CPC .... A61M 5/19; A61M 5/31596; A61M 5/284; A61M 2005/1787
See application file for complete search history.

(56) References Cited

U.S. PATENT DOCUMENTS

| | | |
|---|---|---|
| 4,702,737 A | 10/1987 | Pizzino |
| 5,716,339 A | 2/1998 | Tanaka et al. |
| 6,723,074 B1 * | 4/2004 | Halseth ................ A61M 5/284 604/206 |
| 7,048,720 B1 | 5/2006 | Thorne, Jr. et al. |
| 8,021,343 B2 | 9/2011 | Nalesso et al. |
| 2006/0052747 A1 * | 3/2006 | Nishimura ........ A61M 5/31596 604/86 |
| 2006/0258977 A1 | 11/2006 | Lee |
| 2009/0062740 A1 | 3/2009 | Thorne, Jr. et al. |
| 2014/0296791 A1 | 10/2014 | Wong |

* cited by examiner

*Primary Examiner* — Laura A Bouchelle
*Assistant Examiner* — John A Doubrava
(74) *Attorney, Agent, or Firm* — Stephen Bullock; Bullock Law (57) ABSTRACT

Embodiments of the present invention are related to a multichambered syringe including a main body. The main body may include a body first end, a body second end, and a body housing extending from the body first end to the body second end. Within the body housing may be at least one separating member, a plurality of chambers, and a puncture device. The puncture device may be structured to breach the at least one separating member. The puncture device and the at least one separating member may be structured to form a plurality of guided tunnels when the puncture device and the at least one separating member are engaged.

17 Claims, 9 Drawing Sheets

MULTICHAMBERED SYRINGE

RELATED APPLICATIONS

This application claims the benefit under 35 U.S.C. § 119(e) of U.S. Provisional Patent Application Ser. No. 62/753,401 titled Dyad Syringe filed on Oct. 31, 2018, the entire contents of which are incorporated herein by reference.

FIELD OF THE INVENTION

The present invention relates to systems and methods for administering medication. More particularly, the present invention relates to administering a plurality of fluids through a multichambered syringe.

BACKGROUND

Traditionally, the administration of medication into the circulatory system has involved drawing medication through a first syringe, securing that syringe onto a catheter port, then administering the medication. The administrator subsequently uses a second syringe with a rinsing solution to clear the catheter of stagnant medication.

There exists a need in the art for a more efficient means to deliver medication into the circulatory system. Moreover, there exists a need in the art for a single syringe to hold separately a plurality of solutions before sequentially expressing them.

This background information is provided to reveal information believed by the applicant to be of possible relevance to the present invention. No admission is made as to prior art and nothing within the background should be construed as prior art against the present invention.

SUMMARY OF THE INVENTION

Embodiments of the present invention are related to a multichambered syringe including a main body. The main body may include a body first end, a body second end, and a body housing extending from the body first end to the body second end. Within the body housing may be at least one separating member, a plurality of chambers, and a puncture device. The puncture device may be structured to breach the at least one separating member. The puncture device and the at least one separating member may be structured to form a plurality of guided tunnels when the puncture device and the at least one separating member are engaged.

In this embodiment the at least one separating member may include a receiving sleeve structured to receive the puncture device. The at least one separating member may include a medial membrane structured to be breached by the puncture device. The puncture device may include a plurality of longitudinal channels positioned on the puncture device periphery. Each longitudinal channel of the plurality of longitudinal channels may align with a respective angled end channel of a plurality of angled end channels. The plurality of angled end channels may extend radially from a position proximate a medial aperture in the body second end.

The body housing may be bifurcated between a body housing first part and a body housing second part. The body housing first part may be structured to removably attach to the body housing second part by at least one of threading and friction fit. The body housing first part may include the at least one separating member and the body housing second part may include the puncture device.

Another embodiment may include a multichambered syringe including a main body with a body first end, a body second end, and a body housing extending from the body first end to the body second end. There may be at least one separating member, a puncture device, and a plurality of chambers. The plurality of chambers may include at least a first chamber and at least a second chamber separated by the at least one separating member. The second chamber may include the puncture device. The body housing may include the at least one separating member between the body first end and the body second end. The puncture device may be structured to breach the at least one separating member and the puncture device and the at least one separating member may be structured to fittingly engage one another. The puncture device and the at least, one separating member may be structured to form a plurality of guided tunnels from the first chamber to the body second end when the puncture device has fittingly engaged the at least one separating member.

In this embodiment the at least one separating member may include a receiving sleeve structured to receive the puncture device. More specifically, the receiving sleeve may include a connecting membrane structured to be breached by the puncture device.

The body second end may include a plurality of angled end channels extending radially from a position proximate a medial aperture in the body second end. The body second end may include a plurality of fluid guides. The puncture device may be an elongate member connected perpendicularly to a medial point on the fluid guides at one end and may taper to a point at another end.

The puncture device may include a plurality of longitudinal channels positioned on the puncture device periphery. Each longitudinal channel of the plurality of longitudinal channels may align with a respective angled end channel of a plurality of angled end channels.

In this embodiment the at least one separating member may equal two separating members and the plurality of chambers may equal three chambers.

Another embodiment may include a multichambered syringe including a main body with a body first end, a body second end, and a body housing extending from the body first end to the body second end. There may be at least one separating member with an elongate receiving sleeve structured to receive a puncture device. The separating member may include a connecting membrane within the receiving sleeve, defined as a stopper. There may be a plurality of fluid guides fixedly attached to the body second end and an elongate puncture device fixedly attached to the plurality of fluid guides at one end. The elongate puncture device may extend from the plurality of fluid guides and taper to a point at its opposing end.

This embodiment may include a plurality of chambers with at least a first chamber and at least a second chamber separated by the at least one separating member. The body housing may include the at least one separating member between the body first end and the body second end. The puncture device may be structured to fit within the receiving sleeve. Each respective fluid guide of the plurality of fluid guides may include a side wall that opposes an adjacent side wall of an adjacent fluid guide. The respective side walls of adjacent fluid guides may combine with channel floors to form a plurality of angled end channels extending radially from a position proximate a medial aperture in the body second end.

The puncture device may be oriented perpendicularly to a medial point on the plurality of fluid guides. The puncture device may include a plurality of longitudinal channels positioned on the puncture device periphery. Each longitudinal channel of the plurality of longitudinal channels may align with a respective angled end channel. The puncture device may be structured to breach the stopper of the at least one separating member and may be structured to fittingly engage the at least one separating member. The puncture device and the at least one separating member may be structured to form a plurality of guided tunnels from the first chamber to the body second end when the puncture device has fittingly engaged and breached the at least one separating member.

In this embodiment, one end of the puncture device may include a plurality of arcuate channel second ends forming a plurality of archways that connect from one fluid guide to an adjacent fluid guide. The plurality of archways may circumscribe a syringe opening and form a portion of a lower cavity between the syringe opening and the bottom of the puncture device.

The separating member may be structured to slide within the housing and fully compress the second chamber until the at least one separating member is fittingly engaged with the puncture device. The stopper may be medially positioned within the receiving sleeve and the length of the puncture device from base to tip may be equal to the length of the receiving sleeve.

DETAILED DESCRIPTION OF THE INVENTION

The present invention will now be described in detail with reference to the accompanying drawings. The embodiment descriptions are illustrative and not intended to be limiting in any way. Other embodiments of the invention will readily suggest themselves to persons with ordinary skill in the art after having the benefit of this disclosure. Accordingly, the following embodiments are set forth without any loss of generality and without imposing limitation upon the claimed invention.

Directional terms such as "above" "below" "upper" "lower" and other like terms are used for the convenience of the reader in reference to the drawings. Additionally, the description may contain terminology to convey position, orientation, and direction without departing from the principles of the present invention. Such positional language should be taken in context of the represented drawings.

Quantitative terms such as "generally" "substantially" "mostly" and other like terms are used to mean that the referred object, characteristic, or quality constitutes a majority of the referenced subject. Likewise, use of the terms such as first and second do not necessarily designate a limitation of quantity. Such terms may be used as a method of describing the presence of at least one of the referenced elements or may provide a means of differentiating orientation. The meaning of any term within this description is dependent upon the context within which it is used, and the meaning may be expressly modified.

Figure 1:
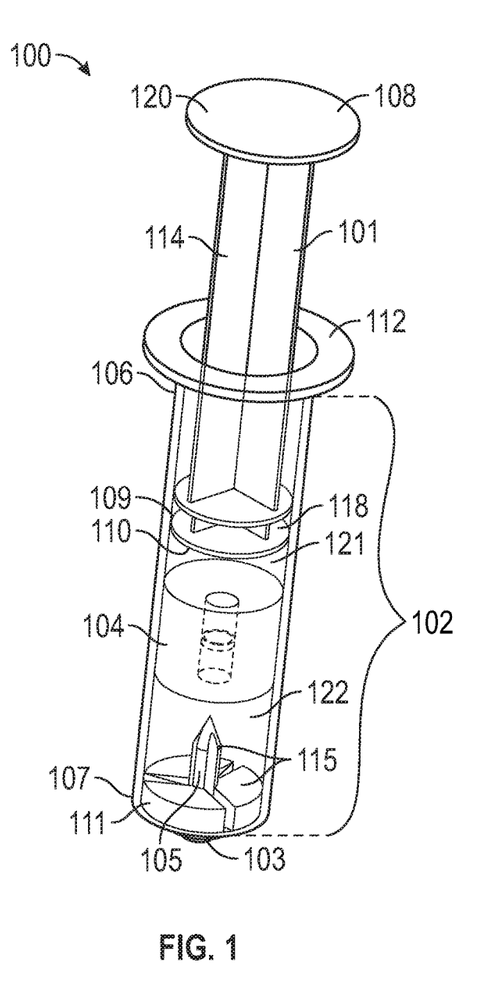
FIG. 1 is a perspective view of a multichambered syringe according to an embodiment of the invention.

Referring now to FIG. 1, a multichambered syringe 100, hereinafter referred to as the syringe 100, will be described. The syringe 100 may include a plunger 101, a body housing 102, and a syringe opening 103.

The plunger 101 may include a plunger first end 108, a plunger shaft 114, and a plunger second end 109. The plunger first end 108 may include a leveraging member 120 structured to facilitate a user applying force with a digit or palm to drive the plunger 101 into and out of the body housing 102. The plunger shaft 114 may be an elongate member extending from the plunger first end 108 to the plunger second end 109. The plunger second end 109 may include opposing surfaces including a dry surface 118 and an engagement surface 110. The plunger shaft 114 may connect to the dry surface 118 and the engagement surface 110 may be oriented to face the internal components of the body housing 102. In some embodiments, the engagement surface 110 may be generally convex with a summit directed toward the internal components of the body housing 102.

The body housing 102 may be an elongate tube structured to contain liquid as well as components of the syringe 100. In some embodiments, the body housing 102 may be cylindrical in shape. The body housing 102 may include a body first end 106 and a body second end 107. The body first end 106 may include a gripping member 112. The gripping member 112 may be used in conjunction with the leveraging member 120 to facilitate a user pushing and pulling the plunger 101 into and out of the body housing 102. The body second end 107 may be proximate the syringe opening 103.

Contained within the body housing 102 may be at least one separating member 104 and a puncture assembly 115. The separating member 104 may be positioned within the body housing 102 between the body first end 106 and the body second end 107. More specifically, the separating member 104 may be positioned between the engagement surface 110 of the plunger 101 and the puncture assembly 115 on the body second end 107. The separating member 104 may be positioned so as to bifurcate the body housing 102 into a plurality of chambers.

As shown by the embodiment in FIG. 1, the body housing 102 may include a first chamber 121 and a second chamber 122. The first chamber 121 may be positioned between the engagement surface 110 of the plunger 101 and the separating member 104. The second chamber 122 may be positioned between the puncture assembly 115 at the second end 107 of the body housing 102 and the separating member 104. The first chamber 121 and the second chamber 122 may be structured to contain liquid therein. More specifically, the separating member 104 may be structured to isolate the liquid within each chamber so that the first chamber 121 may contain a different liquid than the second chamber 122.

Within the second chamber 122 and positioned at the body housing 102 second end 107 may be the puncture assembly 115. The puncture assembly 115 may include a puncture device 105 and a plurality of fluid guides 111. The puncture device 105 may be an elongate member oriented perpendicularly to a medial point proximate the body second end 102 that connects to the plurality of fluid guides 111 at one end and tapers to a point at another end.

A fluid guide 111 may be a pie shaped wedge with its larger semicircular perimeter connected to the inside body housing 102 and a smaller opposing semicircular perimeter connected to the puncture device 105. The fluid guide 111 may also be connected to the body housing 102 second end 107 at one surface and may include an opposing planar surface that faces the second chamber 122 and the separating member 104. It is also contemplated to be within the scope of this application that one embodiment may include the puncture assembly 115 as a separate insert that does not form an attached unit with the body housing 102 second end 107.

Figure 2:
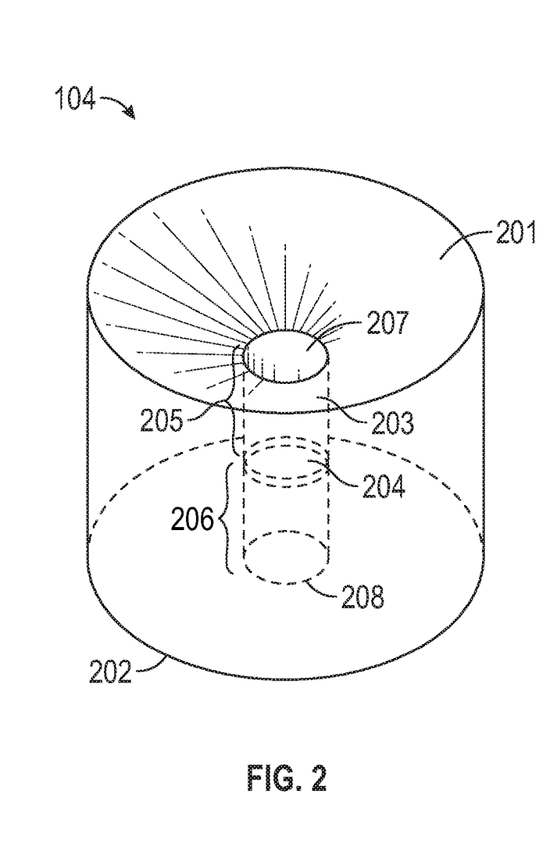
FIG. 2 is a perspective view of a separating member found within the multichambered syringe illustrated in FIG. 1.

Referring to FIG. 2, the separating, member 104 will now be discussed in more detail. As depicted, the separating member 104 may be cylindrical in shape. However, the overall shape of the separating member 104 may conform with the interior of the body housing 102 of the syringe 100. Therefore, a rectangular shaped body housing 102 may include a square, rectangular, or polygonal shaped separating member 104. The diameter of the separating member 104 may equal, or be nominally less, than the inside diameter of the interior walls of the body housing 102. The diameter may be sufficient to prevent the backflow of fluid out of the first chamber 121, but also allow for the separating member to slide within the body housing 102.

The separating member 104 may include a top surface 201, a bottom surface 202, and a receiving sleeve 203 extending from the top surface 201 to the bottom surface 202. In some embodiments, the longitudinal length of the separating member, measured from the top surface 201 to the bottom surface 202 may range between 2 to 15 millimeters for a standard syringe found in the art.

The bottom surface 202 may be flat. However, the top surface 201 may be generally concave to accommodate the generally convex engagement surface 110 of the plunger 101. When engaged with the engagement surface 110, the top surface 201 and the engagement surface 110 may fit together so that their geometric contours fit together. This conformity of shape between the top surface 201 and engagement, surface 110 may facilitate the expulsion of fluid out of the first chamber 121 and through the receiving sleeve 203 when punctured.

The receiving sleeve 203 may be a centrally positioned tunnel within the separating member 104 with a top opening 207 and a bottom opening 208 structured to receive the puncture device 105 therein. The center of the receiving sleeve 203 may align with the apex or point of the puncture device 105. The diameter of the receiving sleeve 203 may equal the largest diameter of the puncture device 105 so that when the puncture device 105 is received, portions of the puncture device 105 may abut the interior walls of the receiving sleeve 203.

Positioned within the receiving sleeve 203 of the separating member 104 may be a medial membrane 204. The medial membrane 204 may extend across the interior walls of the receiving sleeve 203. It may act as a stopper within the receiving sleeve 203 preventing liquid contained in the first chamber 121 from combining, with liquid contained in the second chamber 122 until punctured.

The medial membrane 204 may divide the receiving sleeve 203 into two halves including a first sleeve segment 205 and a second sleeve segment 206. For purposes of this application, the term medial should not be construed as limiting. In some embodiments, the medial membrane 205 may not be centered along a longitudinal length of the receiving sleeve 203. In such instances, the first sleeve segment 206 may not be equal in size to the second sleeve segment 207. The alternative positioning of the medial membrane 204 within the receiving sleeve 203 may allow for slightly altered dosages between the chambers divided by the separating member 104.

The separating member 104 may be made from one or more of several materials including silicone, rubber, plastic, and metal. In some embodiments, the medial membrane 204 may be made of a different material than the remainder of the separating member 104. By way of non-limiting example, the medial membrane 204 may be made of silicone and the remaining portions of the separating member 104 may be made of rubber.

Figure 3A:
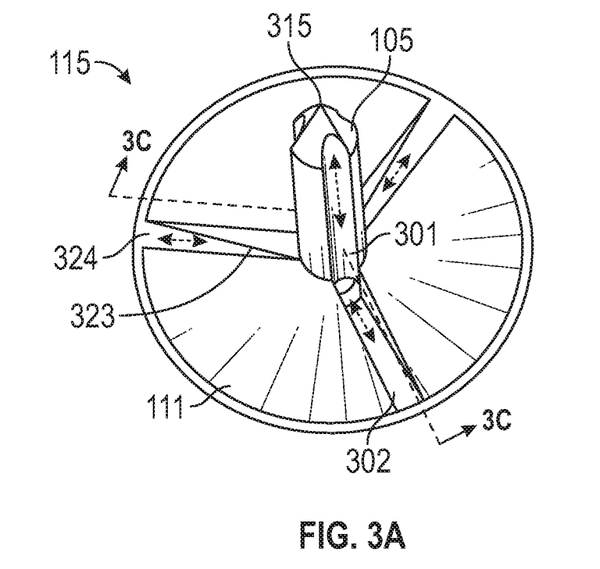
FIG. 3A is a top perspective view of a puncture assembly found within the multichambered syringe illustrated in FIG. 1.
Figure 3B:
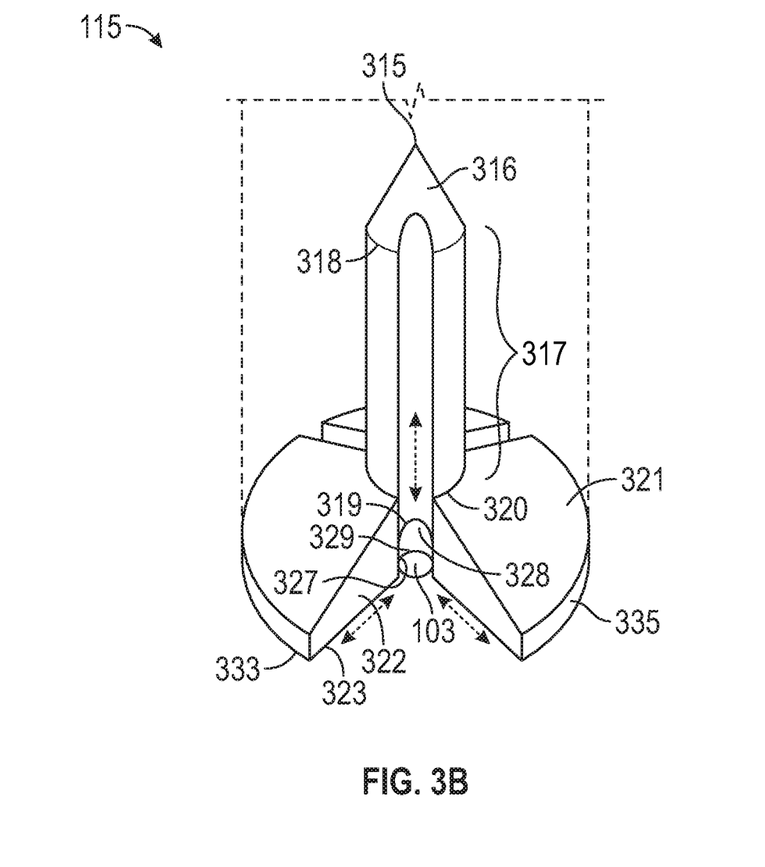
FIG. 3B is a side perspective view of a puncture assembly found within the multichambered syringe illustrated in FIG. 1.

Referring now to FIGS. 3A and 3B, the puncture assembly 115 will be described in more detail. Both figures show an overview of the puncture assembly 115 demonstrating the interconnectivity and interactivity between the puncture device 105 and the fluid guides 111. In some embodiments, the puncture device assembly 115 may be a single unit that connects to the body housing 102 of the syringe 100. The puncture device assembly 115 may be made of the same material as the body housing 102, for example plastic. However, in some embodiments, one or more materials such as rubber, metal, wood, or silicon may be used to form the puncture device assembly. Furthermore, in some embodiments the puncture device assembly 115 may be an unattached insert that fits within the body housing 102.

The puncture device 105 may include a puncture device point 315, a tapered end 316, and a puncture device body 317. The tapered end 316 may be angled or curved from the puncture device point 315 to a device body first end 318. The puncture device body 317 may extend longitudinally from the device body first end 318 and connect to the fluid guides 111.

The puncture device 105 periphery may include a plurality of longitudinal channels 301 that extend from a midpoint on the tapered end 316, run along the puncture device body 317, and end at a plurality of arcuate channel second ends 319. The plurality of arcuate channel second ends 319 may be a plurality of archways that connect from one fluid guide 111 to an adjacent fluid guide 111.

As previously described, a fluid guide 111 may be a pie shaped wedge with a larger semicircular perimeter, defined as the outside perimeter 335 connected to the inside body housing 102. The fluid guide 111 may also include a smaller opposing semicircular perimeter, defined as the inside perimeter 320 connected to the puncture device 105. The fluid guide top surface 321 may be flat and the fluid guide bottom surface 333 may correspond in shape to the body second end 107 of the body housing 102. In some embodiments the fluid guide bottom surface 333 may be angled from the perimeter walls of the body housing 102 at the body second end 107 to the syringe opening 103. In some embodiments the shape may be curved or bulbous. Therefore, the fluid guide top surface 321 may be at a flat or near flat zero-degree or 180-degree angle and the fluid guide bottom surface may be at an angle of 10 to 50 degrees with respect to the interior walls of the body housing 102.

Each fluid guide 111 may include a pair of triangular or near triangular side walls 322. Each side wall 322 may resemble a right triangle with the hypotenuse edge 323 extending from the outside perimeter 335 to the inside perimeter 320. Therefore, when the puncture assembly 115 is oriented as in FIGS. 3A and 3B, the hypotenuse edge 323 of the side wall 322 may descend to a lower central portion of the body second end 107 proximate the syringe opening 103.

Each side wall 322 may face an adjacent side wall 322 of an adjacent fluid guide 111 to form an end channel 302. Each end channel 302 may include two opposing side walls 322 and an angled or curved channel floor 324. Each channel floor 324 may extend from the interior wall of the body housing 102 at the body second end 107 to a central portion of the body second end 107 proximate the syringe opening 103. Therefore, the plurality of end channels 302 may extend radially from a position proximate a medial aperture in the body second end 107.

Each end channel 302 may align with each longitudinal channel 301 of the puncture device 105. Furthermore, each arcuate channel second end 319 of each longitudinal channel 301 may begin at a medial point on the center edge 327 of the side wall 322 and may extend to a medial point on an adjacent center edge 327 of an adjacent side wall 322 to form an archway 328. A plurality of archways 328 may circumscribe the syringe opening 103 and may form a portion of a lower cavity 329 between the syringe opening 103 and the bottom of the puncture device 105. The lower cavity 329 in conjunction with the end channels 302 may facilitate the intake and expulsion of liquid from the syringe opening 103 by providing guided space between the syringe opening 103 and the body housing 102.

Figure 3C:
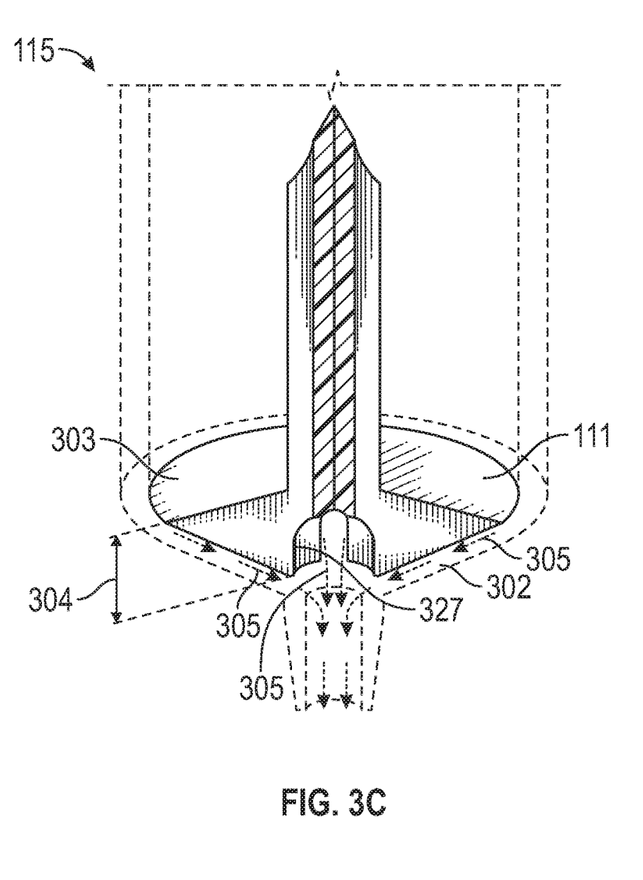
FIG. 3C is a cross-sectional view of the puncture assembly taken through dissecting line 3C of FIG. 3A.
Figure 3D:
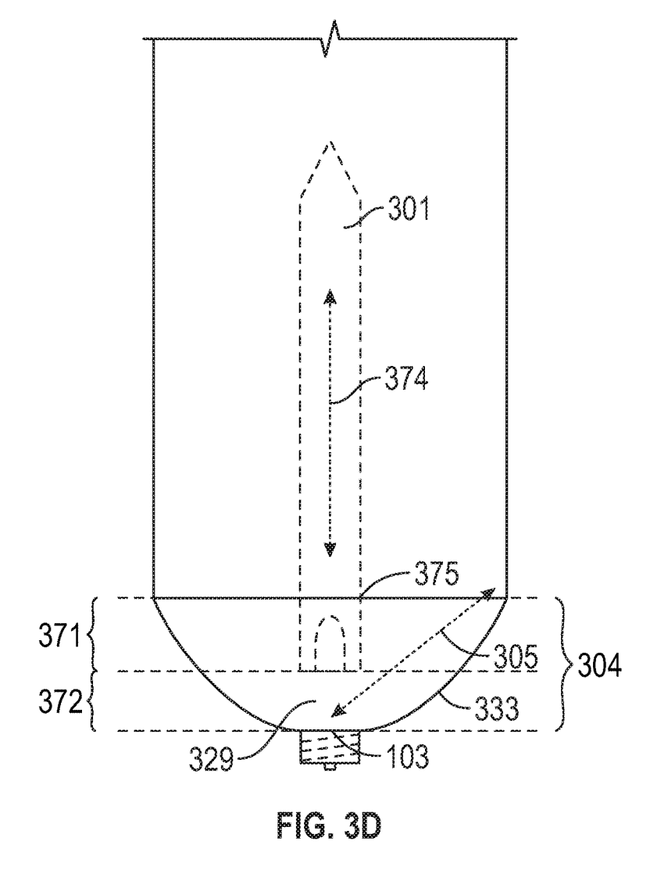
FIG. 3D is a planar view of the puncture assembly found within the multichambered syringe illustrated in FIG. 1.

Referring now to FIGS. 3C and 3D the interactivity between the puncture device 105 and the fluid guides 111 will be described in more detail. FIG. 3C is a cross-sectional view of the puncture assembly 115 taken through dissecting line 3C of FIG. 3A. As demonstrated in FIG. 3C, each fluid guide 111 may contain an angled depth 304 ranging from the fluid guide top surface 303 to the fluid guide center edge 327. The combined angled depth 304 of two adjacent fluid guides 111 along with the angled channel floor 324 may allow for angled fluid flow 305 to ascend or descend the end channel 302.

FIG. 3D illustrates the different levels of the lower portion of the syringe 100 as well as the directional flow of fluid therein. The longitudinal channel 301 of the puncture device 105 may allow for longitudinal fluid flow 374 thereon. When fluid is being drawn into the syringe 100, the longitudinal fluid flow 374 may travel along the longitudinal channels 301 distally from the syringe opening 103 into the body housing 102. When fluid is being expelled out of the syringe 100, the longitudinal fluid flow 374 may travel along the longitudinal channels 301 toward the syringe opening 103.

In some embodiments, the depth 304 of the fluid guides 111 may allow for a multi-tiered lower portion of the syringe 100 including a first level 372 and a second level 372. The beginning of the first level 371 may include the puncture device attachment 375 where the non-channeled portions of the puncture device 105 attach to the fluid guide top surfaces 303. The end of the first level 371 and the bottom of the fluid guide center edge 327 may be the beginning of the second level 372. The second level 372 may include the lower cavity 329 that surrounds the syringe opening 103. The angled fluid flow 305 may flow from the beginning of the first level 371 to the bottom of the first level 372 and the syringe opening 103. When fluid is being drawn into the syringe 100, the angled fluid flow 305 may travel along the end channels 302 distally from the syringe opening 103 into the body housing 102. When fluid is being expelled out of the syringe 100, the angled fluid flow 305 may travel along the end channels 302 toward the syringe opening 103.

Figure 3E:
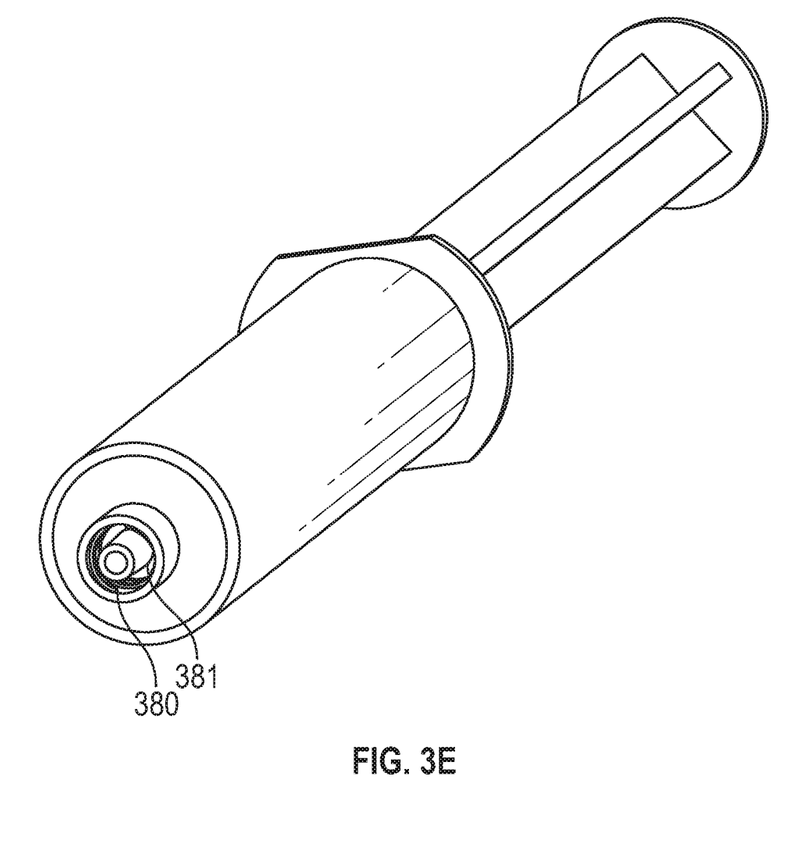
FIG. 3E is a bottom perspective view of the multichambered syringe illustrated in FIG. 1.

FIG. 3E illustrates the outside bottom of the syringe 100. In some embodiments, the syringe 100 may be a luer lock or luer slip type of syringe comprising outer threading 380 and an internal guide tube 381. The combination of the outer threading 380 and internal guide tube 381 may allow for the syringe 100 to easily attach to a catheter. Furthermore, the specific structure of the syringe 100, with the puncture device 105 sitting on top of the fluid guides 111 and removed from the syringe opening 103, facilitates the use of the syringe 100 with catheters and catheter ports.

Figure 4A:
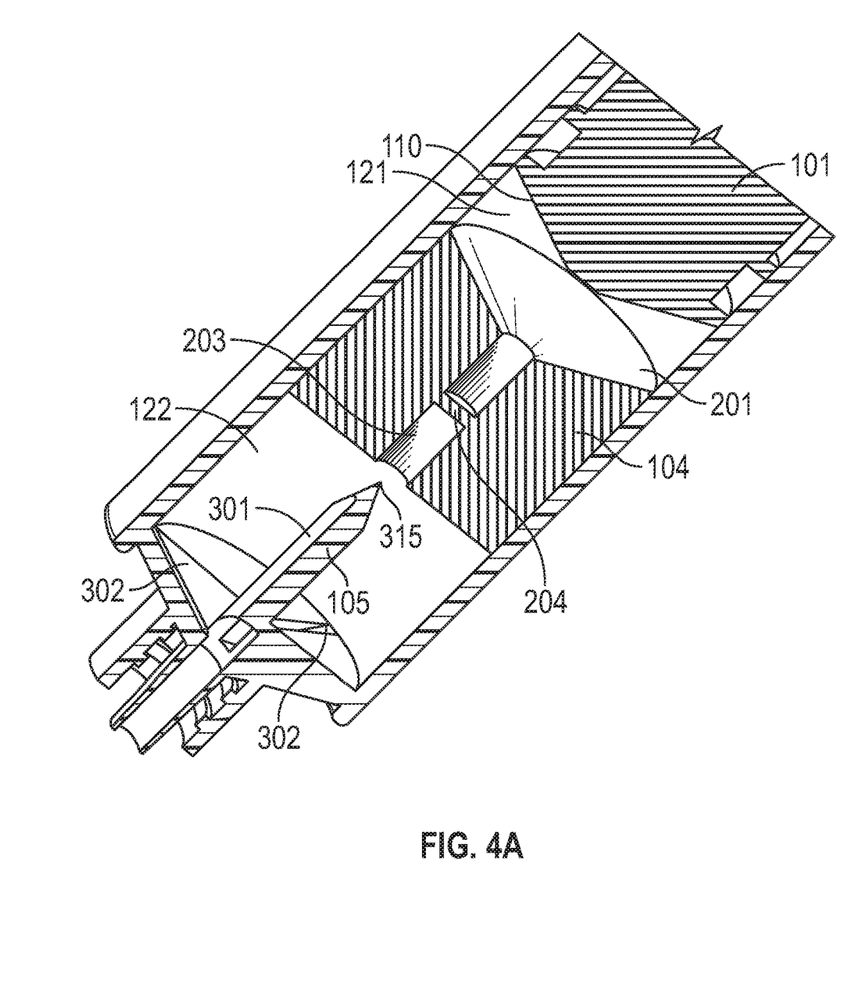
FIG. 4A is a cross-sectional view of a lower portion of the multichambered syringe illustrated in FIG. 1.
Figure 4B:
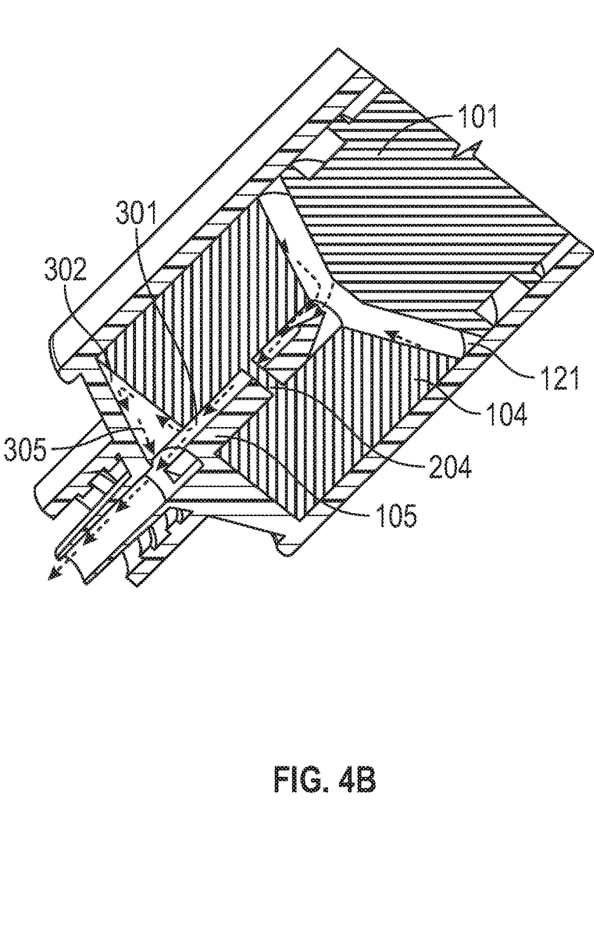
FIG. 4B is a cross-sectional view of a lower portion of the multichambered syringe illustrated in FIG. 1.

Referring to FIGS. 4A and 4B, the functionality of the invention will now be described in more detail. Both figures represent what happens within the lower portion of the syringe 100 when a user is pushing the plunger 101 into the body housing 102 to expel the contents of the chambers.

FIG. 4A is a cross-section of the lower portion of the syringe 100 illustrating the point 315 of the puncture device 105 aligned with the center of the receiving sleeve 203 of the separating member 104. At this stage, the figure represents the engagement surface 110 of the plunger 101 approaching the top surface 201 of the separating member 104 as the plunger 101 is being driven into the body housing 102. Although for clarity purposes the fluid is not shown, the content of the second chamber 122 is being expelled out of the opening 103 and the plunger 101 is moving the first chamber 121 and the separating member 104 in unison toward the puncture device 105. The second chamber 122 is being compressed and depleted, while the first chamber 121 and its contents remain intact.

FIG. 4B Illustrates the stage when the second chamber 122 has been completely depleted and its fluid expelled. As depicted, the puncture device 105 and the receiving sleeve 203 of the separating member 104 are structured to fittingly engage one another. The puncture device 105 has engaged the separating member 104 and breached the medial membrane 204. The remaining fluid of the first chamber 121 is being pushed out of the syringe 100 as the first chamber 121 is compressing.

The fluid of the first chamber 121 at this stage is travelling within the receiving sleeve 203 toward the syringe opening 103. The puncture device 105 is completely surrounded by the receiving sleeve 203 and the medial membrane 204. Therefore, the fluid of the first chamber 121 is being directed down the receiving sleeve 203, along the longitudinal channel 301 and through the medial membrane 204 as it is being expelled out of the syringe 103. After exiting the second sleeve segment 206, some of the fluid from the first chamber 121 takes a direct path down the longitudinal channel 301 and out the syringe opening 103. However, after exiting the second sleeve segment 206, some of the fluid from the first chamber 121 is flushed through the end channels 302 as angled fluid flow 305 before exiting the syringe opening 103.

Figure 5A:
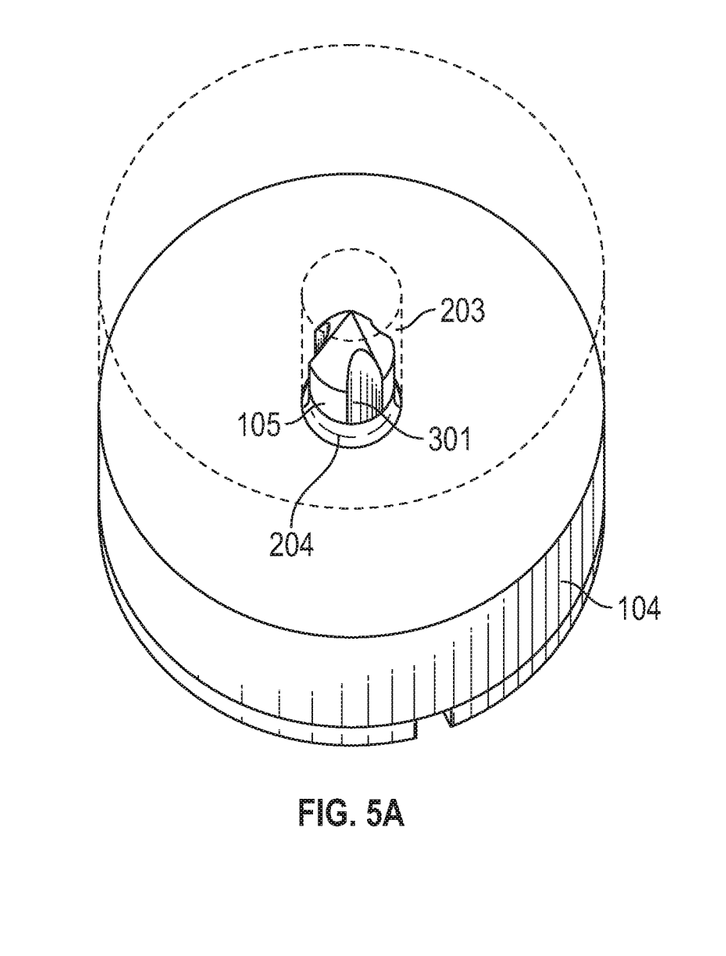
FIG. 5A is a partially transparent cross-sectional view of a punctured separating member illustrated in FIG. 2.
Figure 5B:
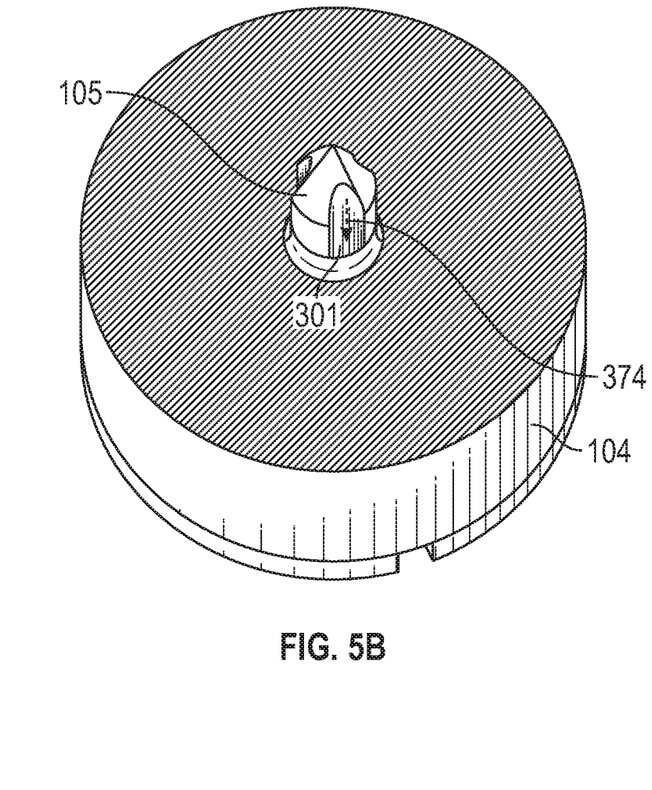
FIG. 5B is a partial cross-sectional view of a punctured separating member illustrated in FIG. 2.

FIGS. 5A and 5B illustrate the puncture device 105 within the receiving sleeve 203 surrounded by the medial membrane 204 once it has been breached. As illustrated, the combination of the medial membrane 204 and the longitudinal channels 301 make a tunnel for the longitudinal fluid flow 374 to travel through.

Figure 5C:
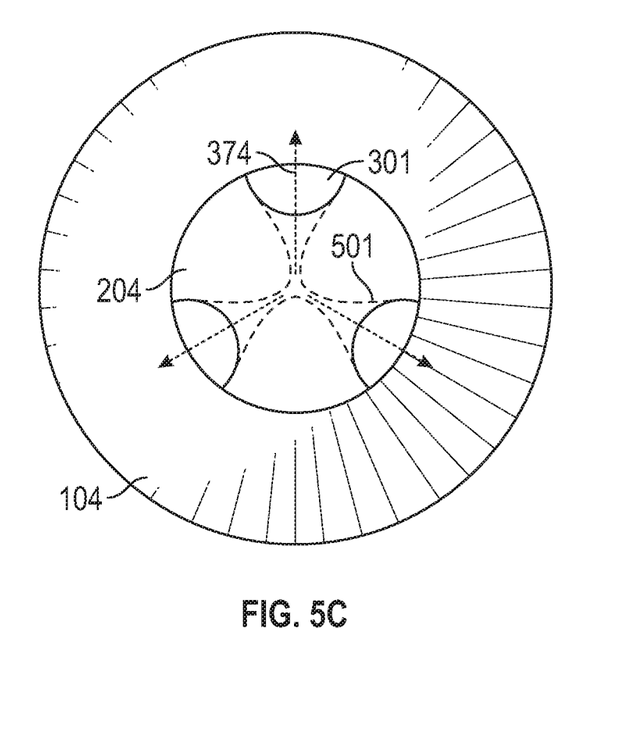
FIG. 5C is a bottom view of a punctured separating member illustrated in FIG. 2.

FIG. 5C illustrates the guided tunnels 501 from a cross-sectional bottom view of the separating member 104 taken through the medial membrane 204 after it has been breached by the puncture device 105. The longitudinal fluid flow 374 as illustrated is descending toward the viewer through the guided tunnels 501 as the longitudinal fluid flow 374 makes its way to the syringe opening 103. The figure clarifies that the puncture device 105 and the separating member 104 are structured to form the plurality of guided tunnels 501 that flow from the first chamber 121 to the body second end 107 when the puncture device 105 has fittingly engaged the separating member 104.

Figure 6A:
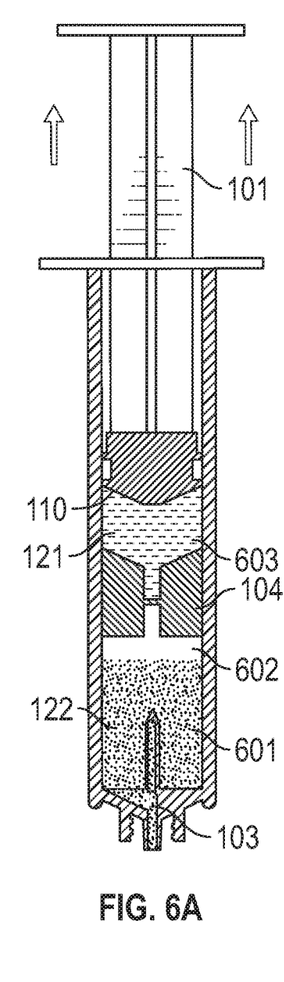
FIG. 6A is a cross-sectional view of the multichambered syringe illustrated in FIG. 1.
Figure 6B:
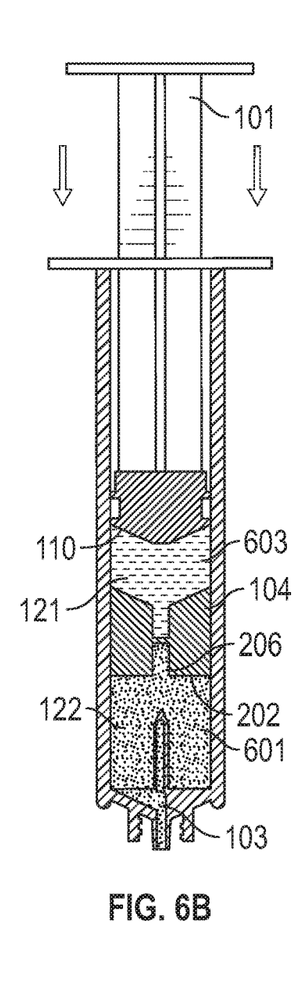
FIG. 6B is a cross-sectional view of the multichambered syringe illustrated in FIG. 1.
Figure 6C:
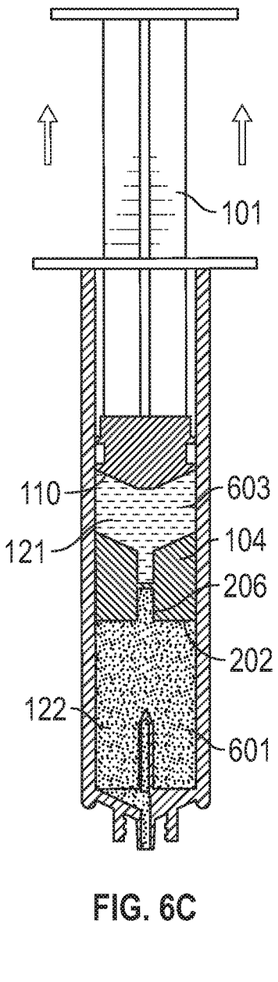
FIG. 6C is a cross-sectional view of the multichambered syringe illustrated in FIG. 1.

FIGS. 6A, 6B, and 6C illustrate what happens internally to the syringe 100 when a user is drawing fluid into the second chamber 122. The syringe 100 may be pressurized to allow the plunger 101 to push and pull the first chamber 121 and the separating member 104 as a single unit. This pressurized system within the body housing 102 may also allow for the separating member 104 to push and pull fluid in and out of the second chamber 122 through the syringe opening 103.

By way of non-limiting example, the first chamber 121 may be prefilled with a fluid such as saline 603. The saline 603 may completely fill the first chamber 121 so that the saline 603 and the engagement surface 110 of the plunger 101 are engaged. When a user pulls the plunger 101 it may pull the first chamber 121 and the separating member 102 in the same direction. When the separating member 102 pulls in a direction distal to the syringe opening 103 medication 601 may draw into the syringe 100 and begin filling the second chamber 122.

As illustrated in FIG. 6A, when a user initially draws medication 601 into the second chamber 122, there may be an air gap 602 between the medication 601 and the separating member 104 within the second chamber 122.

As illustrated in FIG. 6B, because the plunger 101, the first chamber 121, and the separating member 104 are acting as a single unit within the pressurized body housing 102, a user may drive the plunger 101 in a direction toward the syringe opening 103 to bring the bottom surface 202 of the separating member 104 and the second sleeve segment 206 in contact with the medication 601. This may force out the air gap 602 and create a pressurized system with the medication 601 to once again draw medication 601 into the second chamber 122 without the air gap 602.

FIG. 6C illustrates a user once again drawing medication 601 into the second chamber 122 only now without the air gap 602. The pressurized system within the body housing 102 may allow for a user to maneuver the plunger 101 back and forth, as shown in FIGS. 6A, 6B, and 6C as much as needed to remove unwanted air gaps 602 and fill the second chamber 122 with as much medication 601 as desired.

FIGS. 6D to 6G illustrate how the plurality of chambers and the internal components of the syringe 100 function to expel fluids out of the syringe 100.

Figure 6D:
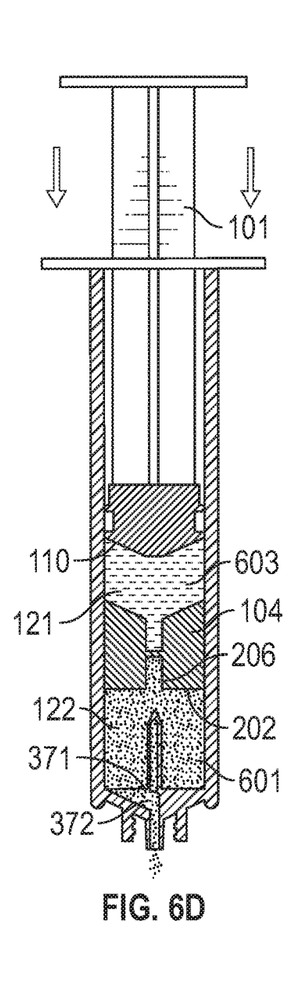
FIG. 6D is a cross-sectional view of the multichambered syringe illustrated in FIG. 1.

FIG. 6D shows that once the desired amount of medication has been drawn into the second chamber 122, a user may then drive the plunger 101 into the body housing 102 to begin expelling the medication 601. The medication 601 may travel through the first level 371 and second level 372 before exiting the syringe opening 103. This figure shows the separating, member 104 approaching the puncture device 105 as the medication 601 is being forced out of the syringe 100.

Figure 6E:
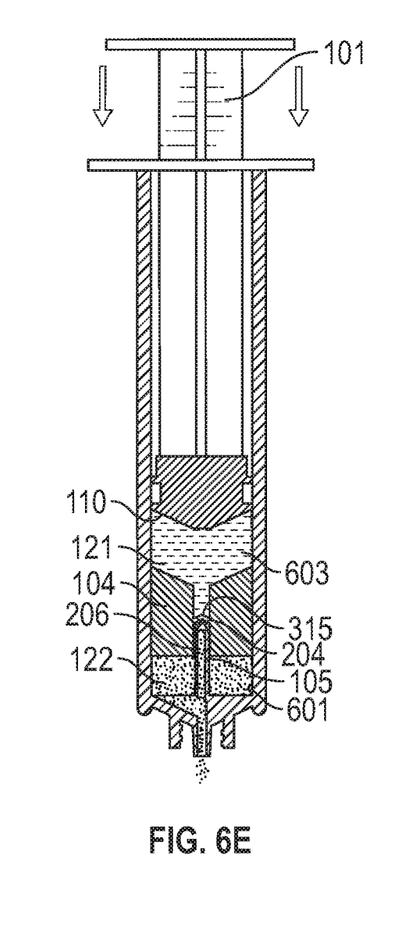
FIG. 6E is a cross-sectional view of the multichambered syringe illustrated in FIG. 1.

FIG. 6E shows the puncture device 105 after having entered the receiving sleeve 203 of the separating member 104 and the point 315 of the puncture device 105 beginning to breach the medial membrane 204 within>the receiving sleeve 203. At this stage, the second chamber 122 has been compressed and there only remains a small amount of medication 601 to be expelled therefrom.

Figure 6F:
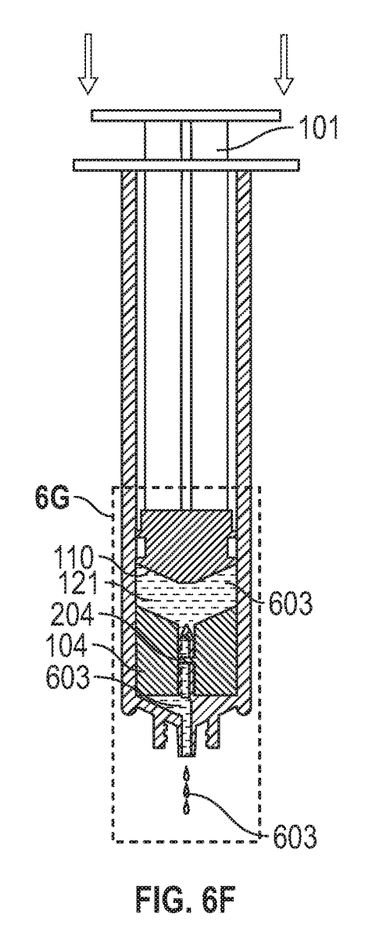
FIG. 6F is a cross-sectional view of the multichambered syringe illustrated in FIG. 1.

FIG. 6F shows the puncture device 105 after completely breaching the medial membrane 204 of the separating member 104. The second chamber 122 and its medication 602 has been completely compressed and no longer remains. The first chamber 121 containing the saline 603 is now being compressed by the engagement surface 110 of the plunger 101 and the saline 603 is being forced down the longitudinal channels 301 and the end channels 302.

Figure 6G:
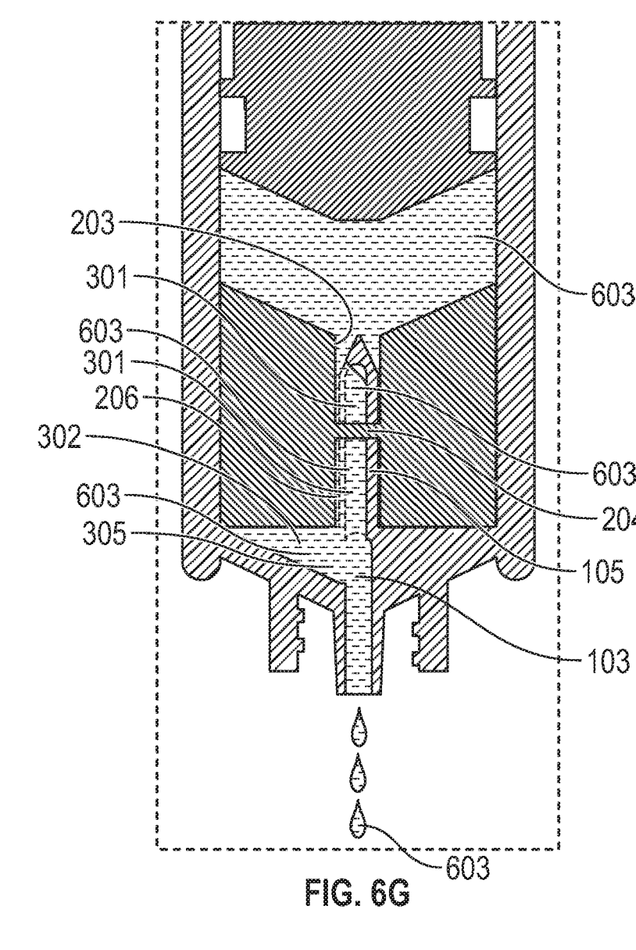
FIG. 6G is an enlarged cross-sectional view of a portion of the multichambered syringe illustrated in FIG. 6F.

FIG. 6G is an enlarged depiction of the lower portion of the syringe 100 to better illustrate the expulsion of the saline 603 in the final, stage. The fluid of the first chamber 121 at this stage is travelling within the receiving sleeve 203 toward the syringe opening 103. The puncture device 105 is completely surrounded by the receiving sleeve 203 and the medial membrane 204. The saline 603 in the first chamber 121 is being directed down the receiving sleeve 203, along the longitudinal channel 301 and through the medial membrane 204 as it is being expelled out of the syringe opening 103. After exiting the second sleeve segment 206, same of the saline 603 from the first chamber 121 takes a direct path down the longitudinal channel 301 and out the syringe opening 103. However, some of the saline 603 from the first chamber 121 is flushed through the end channels 302 as angled fluid flow 305 before exiting the syringe opening 103.

Although the depicted embodiments of this invention illustrate a single separating member 104 with two chambers, it is contemplated to be within the scope of this application that the syringe 100 may include a plurality of separating members 104 and more than two chambers. As illustrated and described in the above embodiments, the puncture device 105 may have a length from the puncture device attachment 375 to the point 315 equal to the length of the receiving sleeve 203. However, by way of non-limiting example, the puncture device 105 may be extended longer than illustrated and the separating member 104 may be thinner than illustrated. In this embodiment, the puncture device 105 may be operable to pierce a plurality of separating members 104 thereby compressing and expelling the contents of more than two chambers.

Furthermore, the current embodiments illustrate the plurality of end channels 302 and the plurality of longitudinal channels 301 as being three respectively. However, it is contemplated to be within the scope of this invention that the number of end channels 302 and longitudinal channels 301 may be one or more respectively. Therefore, it is contemplated that there may be one, two, three, four or more longitudinal channels 301 corresponding with end channels 302. As a consequence, there may be more or less fluid guides 111 to create the end channels 302. By way of non-limiting example, there may be one fluid guide 111 with one end channel 302, There may also be four fluid guides 111 with four end channels 302.

It is also contemplated to be within the scope of the present application that the body housing 102 of the syringe 100 may be modularized so as to be assembled if necessary. In such an embodiment, the syringe body housing 102 may include two halves that are removably engaged to each other. By way of non-limiting example, a first half of the body housing 102 may include side walls with a male threading. The second half of the body housing 102 may include side walls with female threading. The two halves may be structured so as to secure to each other. Other modes of securing to each other may be friction fit or snap fit. It is contemplated that a snap fit may include one end of the body housing with a fastening aperture and the other half including a compressible member that fits within the aperture when decompressed.

A modularized syringe 100 may facilitate manufacturing in that the syringe 100 may be assembled by having the puncture assembly 115 placed within the second chamber 122 before fastening to the rest of the body housing 102. Furthermore, modularizing the body housing 102 may allow for the first chamber 121 to be pre-filled with a solution and locked into place by the separating member 104. The portion of the body housing 102 including the pre-filled first chamber 121 and the separating member 104 may then be assembled with the second half of the body housing 102 that would include the puncture assembly 115.

It is also contemplated to be within the scope of this invention that the plunger 101 is removable. In this embodiment, the plunger 101 may removably engage from the body housing 102 to allow a user to fill the first chamber 121 with fluid before reinserting the plunger 101 into the body housing 102.

That which is claimed is:

1. A multichambered syringe comprising:
   a main body comprising
      a body first end,
      a body second end, and
      a body housing extending from the body first end to the body second end;
   at least one separating member;
   a plurality of chambers;
   a plurality of fluid guides; and
   a puncture device;
   wherein the puncture device is configured to breach the at least one separating member; and
   wherein the puncture device and the at least one separating member are configured to form a plurality of guided tunnels when the puncture device and the at least one separating member are engaged; and
   wherein one end of the puncture device comprises a plurality of arcuate channel second ends, each arcuate channel second end forming an archway that connects one fluid guide to another fluid guide of the plurality of fluid guides.

2. The multichambered syringe of claim 1 wherein the at least one separating member comprises a receiving sleeve configured to receive the puncture device.

3. The multichambered syringe of claim 1 wherein the at least one separating member comprises a medial membrane configured to be breached by the puncture device.

4. The multichambered syringe of claim 1 wherein the puncture device comprises a plurality of longitudinal channels positioned on the puncture device periphery.

5. The multichambered syringe of claim 1, wherein the body housing comprises a first part with at least one separating member and the body housing comprises a second part with the puncture device.

6. The multichambered syringe of claim 4 wherein each longitudinal channel of the plurality of longitudinal channels aligns with a respective angled end channel of a plurality of angled end channels; and wherein the plurality of angled end channels extends radially from a position proximate a medial aperture in the body second end.

7. A multichambered syringe comprising:
   a main body comprising
      a body first end,
      a body second end, and
      a body housing extending from the body first end to the body second end;
   at least one separating member;
   a puncture device;
   a plurality of fluid guides; and
   a plurality of chambers;
   wherein the plurality of chambers comprises at least a first chamber and at least a second chamber separated by the at least one separating member;
   wherein the second chamber comprises the puncture device;
   wherein the body housing comprises the at least one separating member between the body first end and the body second end;
   wherein the puncture device is configured to breach the at least one separating member;
   wherein the puncture device and the at least one separating member are configured to fittingly engage one another;
   wherein the puncture device and the at least one separating member are configured to form a plurality of guided tunnels from the first chamber to the body second end when the puncture device has fittingly engaged the at least one separating member; and
   wherein one end of the puncture device comprises a plurality of arcuate channel second ends, each arcuate channel second end forming an archway that connects one fluid guide to another fluid guide of the plurality of fluid guides.

8. The multichambered syringe of claim 7 wherein the at least one separating member comprises a receiving sleeve configured to receive the puncture device; and wherein the receiving sleeve comprises a connecting membrane configured to be breached by the puncture device.

9. The multichambered syringe of claim 7 wherein the body second end comprises a plurality of angled end channels extending radially from a position proximate a medial aperture in the body second end.

10. The multichambered syringe of claim 7 wherein the body second end comprises the plurality of fluid guides; and wherein the puncture device is an elongate member tapered to a point at one end and at the opposing end is connected to the plurality of fluid guides and oriented along a medial longitudinal axis of the housing.

11. The multichambered syringe of claim 7 wherein the puncture device comprises a plurality of longitudinal channels positioned on the puncture device periphery.

12. The multichambered syringe of claim 7 wherein each longitudinal channel of the plurality of longitudinal channels aligns with a respective angled end channel of a plurality of angled end channels.

13. A multichambered syringe comprising:
   a main body comprising
      a body first end,
      a body second end, and a body housing extending from the body first end to the body second end;
at least one separating member comprising
an elongate receiving sleeve configured to receive a puncture device, and
a connecting membrane within the receiving sleeve, defined as a stopper;
a plurality of fluid guides fixedly attached to the body second end;
an elongate puncture device fixedly attached to the plurality of fluid guides at one end and tapered to a point at another end;
a plurality of chambers;
wherein the plurality of chambers comprises at least a first chamber and at least a second chamber separated by the at least one separating member;
wherein the body housing comprises the at least one separating member between the body first end and the body second end;
wherein the puncture device is configured to fit within the receiving sleeve;
wherein each respective fluid guide of the plurality of fluid guides comprises a side wall that opposes an adjacent side wall of an adjacent fluid guide;
wherein respective side walls of adjacent fluid guides combine with channel floors to form a plurality of angled end channels extending radially from a position proximate a medial aperture in the body second end;
wherein the puncture device is connected to the plurality of fluid guides and oriented along a medial longitudinal axis of an interior of the housing;
wherein the puncture device comprises a plurality of longitudinal channels positioned on the puncture device periphery;
wherein each longitudinal channel of the plurality of longitudinal channels aligns with a respective angled end channel;
wherein the puncture device is configured to breach the stopper of the at least one separating member;
wherein the puncture device and the at least one separating member are configured to fittingly engage one another; and
wherein the puncture device and the at least one separating member are configured to form a plurality of guided tunnels from the first chamber to the body second end when the puncture device has fittingly engaged and breached the at least one separating member;
wherein one end of the puncture device comprises a plurality of arcuate channel second ends, each arcuate channel second end forming an archway that connects one fluid guide to another fluid guide of the plurality of fluid guides.

14. The multichambered syringe of claim 13 wherein the plurality of archways circumscribes a syringe opening and form a portion of a lower cavity between the syringe opening and the bottom of the puncture device.

15. The multichambered syringe of claim 13 wherein the at least one separating member is configured to slide within the housing and fully compress the second chamber until the at least one separating member is fittingly engaged with the puncture device.

16. The multichambered syringe of claim 13 wherein the stopper is medially positioned within the receiving sleeve.

17. The multichambered syringe of claim 13 wherein the puncture device comprises a length from base to tip equal to a length of the receiving sleeve.

* * * * *